(12) United States Patent
Bastings et al.

(10) Patent No.: US 7,825,285 B2
(45) Date of Patent: Nov. 2, 2010

(54) GLYCOL SEPARATION AND PURIFICATION

(75) Inventors: Roel Guillaume Hubertus Leonardus Bastings, Amsterdam (NL); Anton Pieter Westerink, Amsterdam (NL)

(73) Assignee: Shell Oil Company, Houston, TX (US)

( * ) Notice: Subject to any disclaimer, the term of this patent is extended or adjusted under 35 U.S.C. 154(b) by 699 days.

(21) Appl. No.: 11/761,759

(22) Filed: Jun. 12, 2007

(65) Prior Publication Data

US 2008/0081933 A1    Apr. 3, 2008

(30) Foreign Application Priority Data

Jun. 13, 2006   (EP) .................... 06253031

(51) Int. Cl.
*C07C 27/00* (2006.01)
(52) U.S. Cl. ...................... 568/858; 549/230
(58) Field of Classification Search ................. 568/858; 549/230
See application file for complete search history.

(56) References Cited

U.S. PATENT DOCUMENTS

| | | | |
|---|---|---|---|
| 4,143,521 A | 3/1979 | Pano et al. ..................... 62/101 |
| 4,283,580 A | 8/1981 | Odanaka et al. ............. 568/858 |
| 4,400,559 A | 8/1983 | Bhise .......................... 568/858 |
| 4,530,826 A | 7/1985 | Ohashi et al. ................ 423/376 |
| 5,231,212 A | 7/1993 | Buysch et al. ............... 558/277 |
| 6,080,897 A | 6/2000 | Kawabe ....................... 568/858 |
| 6,187,972 B1 | 2/2001 | Kawabe et al. .............. 568/858 |
| 6,537,458 B1 | 3/2003 | Polderman ................... 210/801 |

FOREIGN PATENT DOCUMENTS

| | | |
|---|---|---|
| DE | 1031285 | 6/1958 |
| EP | 1484300 A1 | 12/2004 |
| WO | WO 9823351 | 6/1998 |
| WO | WO 0117935 | 3/2001 |

*Primary Examiner*—Elvis O Price

(57) ABSTRACT

A process and an apparatus for the separation of a homogeneous catalyst solution from crude monoethylene glycol (MEG) and for purifying MEG is disclosed. The process comprises separating catalyst solution by evaporating crude MEG and feeding crude MEG to a rectification section, a stripping section, and thence to a pasteurisation section, each section operated at subatmospheric pressure of $0.5 \times 10^5$ $Nm^{-2}$ or less, the rectification and pasteurisation sections being at pressure less than that of the catalyst separation section, wherein the process provides a pressure differential across the catalyst separation and rectification sections and wherein vapour phase crude MEG from the catalyst separation section is fed as substantially vapour phase feed to the rectification section. The apparatus comprises a catalyst separation section, an MEG rectification section, a stripping section and a pasteurisation section, wherein the MEG rectification and pasteurisation sections are located within a MEG purification column, and the catalyst separation section is either located in the MEG purification column or in a separate upstream vessel, and wherein the separation section provides a crude MEG feed inlet to the MEG rectification section and an outlet for separated catalyst, wherein the crude MEG feed inlet to the MEG rectification section is a vapour feed inlet.

12 Claims, 3 Drawing Sheets

GLYCOL SEPARATION AND PURIFICATION

CROSS-REFERENCE TO RELATED APPLICATIONS

This application claims the benefit of European Patent Application No. 06253031.6, filed Jun. 13, 2006, which is incorporated herein by reference.

FIELD OF THE INVENTION

The present invention relates to an apparatus and process for separating catalyst from crude monoethylene glycol (MEG) product and purifying MEG; and the use thereof in an ethylene oxide (EO)/ethylene glycol (EG) plant.

BACKGROUND OF THE INVENTION

MEG is predominantly used for the manufacture of polyester fibres, polyethylene terephthalate (PET) and, to a lesser extent, in the cooling systems of motor vehicles where it serves as antifreeze.

MEG may be produced by the homogeneously catalysed conversion of EO to EG, directly catalysed by e.g. bicarbonate or metalate salts. Alternatively, MEG may be produced by a 2 step process, a ketal type process (catalysed by acids) or via ethylene carbonate (EC) catalysed by e.g. alkali or alkaline earth metal halide, zinc, tin, alkyl amine or quaternary ammonium or the like. In the case of the latter, the integrated EO/EG process is usually split up into four sections: EO reaction and $CO_2$ removal plus EO recovery; Light ends (LE) removal and EO purification; EC/EG reaction and EG recovery; and MEG purification. In the EC/EG reaction section, EO is reacted with $CO_2$ to EC in the presence of a homogeneous catalyst. EC and catalyst are provided to a hydrolysis section in which EC is hydrolysed to MEG in the presence of catalyst, and catalyst is separated from MEG for recycle to the EC/EG reaction section.

In U.S. Pat. No. 6,080,897, a process is shown in which a catalyst separation vessel separates MEG from catalyst by evaporation of MEG, and evaporated MEG is subsequently condensed again to provide a liquid MEG feed to a main MEG purification column for stripping, rectification and pasteurisation. In a process of this type, the MEG purification column operates at a higher pressure than the separation vessel and a pump or gravity force is required to transport the condensed MEG to the MEG purification column.

The disadvantage of this system is that the MEG stream needs to be evaporated twice incurring a high steam requirement. We have now found that a very significant steam saving and investment saving can be made by limiting the process to a single MEG stream evaporation, by omitting the MEG condensation and lowering the operating pressure of the MEG purification column which enables transport of vapours from the catalyst separation section to the MEG purification without the use of a mechanical transport device.

SUMMARY OF THE INVENTION

Accordingly, in the broadest aspect of the invention, there is provided a process for the separation of a homogeneous catalyst solution from crude MEG and for purifying MEG, for use in a process for the catalytic conversion of EO to MEG, which process comprises separating the catalyst solution in a catalyst separation section by evaporating crude MEG; and purifying the crude MEG by feeding the crude MEG to a rectification section, a stripping section, and thence to a pasteurisation section, wherein each section is operated at subatmospheric pressure of $0.5 \times 10^5$ $Nm^{-2}$ or less, the rectification and pasteurisation sections being at pressure less than that of the catalyst separation section; the process provides a pressure differential between the catalyst separation and rectification sections; and the vapour phase crude MEG from the catalyst separation section is fed as substantially vapour phase feed to the rectification section.

In a first preferred embodiment the separation, rectification and pasteurisation sections operate with internal feeds in open pressure communication between the sections and the stripping section is operated as a side stripping section at subatmospheric pressure greater than the pressure of the rectification section, with external feed in open pressure communication with the rectification section. Condensed liquids from the rectification section are fed externally to the stripping section. The stripped MEG vapours are then returned externally to in between the separation and rectification sections.

Alternatively, in a second embodiment, the stripping, rectification and pasteurisation sections operate with internal feeds in open pressure communication between the sections and the stripping section is installed below the rectification section. In this embodiment, the catalyst separation section is operated with external feed in open pressure communication with the rectification section. The vapour phase crude MEG from the separation section is preferably fed externally to in between the stripping and rectification sections.

Reference herein to open pressure communication is to operation without the use of means to create pressure differential over and above those created by the operation of the sections themselves, e.g in nozzles, internals and the like.

In a further aspect of the invention, there is provided a MEG purification apparatus for the separation of a homogeneous catalyst solution from crude MEG and for purifying MEG, for use in a unit for the catalytic conversion of EO to MEG, which apparatus comprises a catalyst separation section, a rectification section, a stripping section and a pasteurisation section, wherein the rectification and pasteurisation sections are located within a MEG purification column, and the catalyst separation section is either located in the MEG purification column or in a separate upstream vessel; the separation section provides a crude MEG feed inlet to the rectification section and an outlet for separated catalyst; and the crude MEG feed inlet to the rectification section is a vapour feed inlet. The stripping section is either located in the MEG purification column or as a side stripper.

In a first preferred embodiment, the catalyst separation section is located in the MEG purification column below an inlet for introducing liquid phase homogeneous catalyst solution in crude MEG into the catalyst separation section; the rectification and pasteurisation sections are located above the inlet within the same MEG purification column; and the crude MEG feed inlet from the separation section to the rectification section is an internal vapour feed inlet.

In this preferred embodiment, the stripping section is provided as a side stripper comprising an inlet fed by a condensed liquid outlet from the rectification section, and having a vapour phase outlet returning to the internal crude MEG vapour feed inlet from the catalyst separation section to the rectification section.

In a second embodiment, the catalyst separation section is located in a separate vessel upstream of the MEG purification column and the crude MEG feed inlet from the separation section to the rectification section is an external vapour feed inlet, more preferably a side entry vapour feed inlet. In this embodiment, the stripping section is provided in the MEG purification column below the rectification section.

In a further aspect of the invention, there is provided the use of an apparatus or process of the present invention in a unit or process for the catalytic conversion of EO to MEG, preferably an EO/EG plant in which MEG is present with catalyst as hereinbefore described.

Although systems are known, e.g. from U.S. Pat. No. 6,080,897, for the separation of catalyst solution from crude MEG with purification of MEG by sequential distillation typically in two distillation columns, there is no system which operates low pressure separation of catalyst solution from crude MEG with purification of MEG in one column or in a separate MEG purification column and separate upstream catalyst separation vessel, and which also includes flashed glycols feed into the rectification section taking advantage of the generation of MEG vapour in the first separation section for use in the second rectification section without condensing crude MEG after separation and before feeding to the rectification section. This produces a net energy saving and avoids the need for intermediate accumulation and transport equipment for the condensed crude MEG, compared to the known process which operates an intermediate condensation section to enable feed of liquid crude MEG to the higher pressure rectification and stripping section where it is once again vaporised. In addition, this allows the stripping section to handle lower liquid and vapour loading than the liquid and vapour loading of the rectification and pasteurisation sections in the MEG purification column. In a further advantage, the present invention operates without the use of a mechanical transport device between the catalyst separation and rectification section to transport condensed liquid between the sections, in contrast to the known process. Overall this results in benefits in terms of operating costs and plant construction cost.

The invention also allows reduced temperature MEG handling, and reduced temperature catalyst handling in the catalyst separation section by operating at a lower pressure. An additional benefit of operating at the lower pressure is that MEG recovery in the MEG purification column is facilitated further which allows for a higher recovery of the energy in the MEG purification section and a reduced MEG recycle. The feed of crude MEG as vapour to the MEG purification column combined with the higher selectivity of the catalytic glycol production process leads to a reduced size of the stripping section of the MEG purification column of the invention. A more compact equipment design may thereby be realized in the preferred embodiment by installing the rectification and pasteurisation section of the MEG purification column on top of the catalyst separation section, and installing the stripping section as a side stripper next to the rearranged MEG purification column, fed by a draw off tray installed between the catalyst separation and rectification sections. Overall this results in benefits in terms of operating costs and plant construction cost.

DETAILED DESCRIPTION OF THE INVENTION

Figure 1:
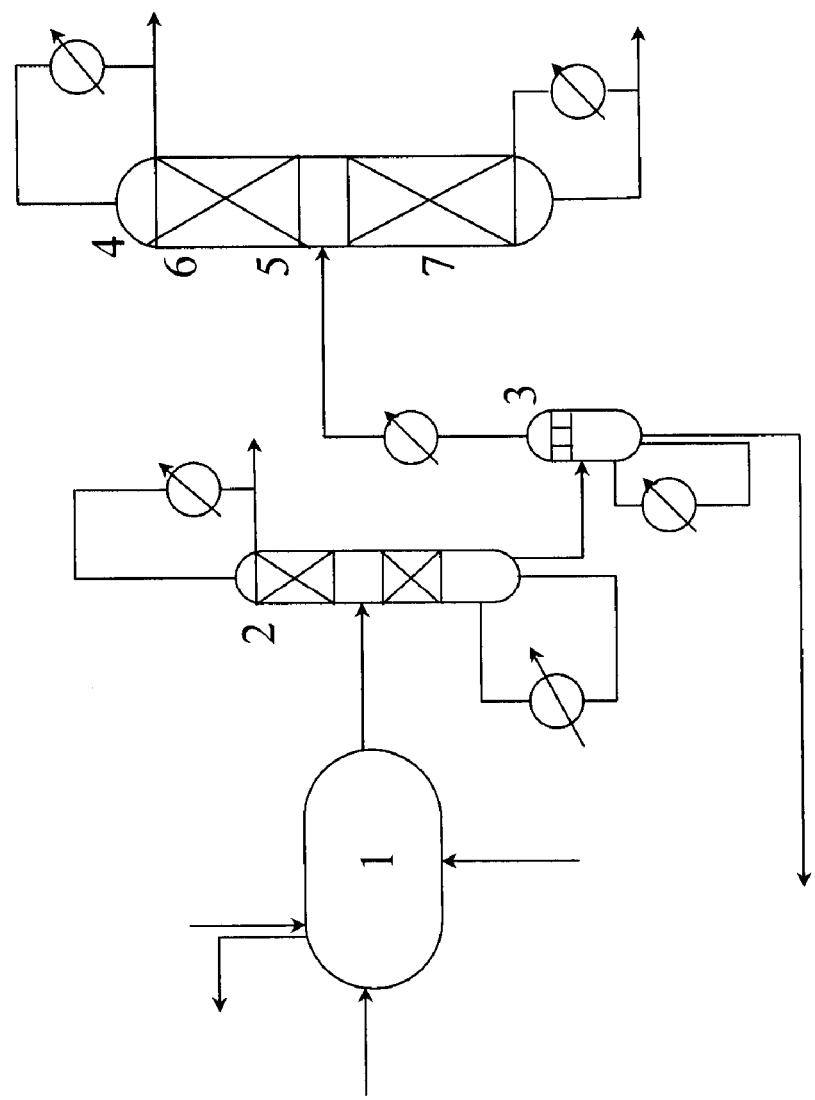
FIG. 1 illustrates a MEG purification process and apparatus as shown in U.S. Pat. No. 6,080,897.

Typically the process and apparatus of the invention separate catalyst solution derived from a glycol dehydrator section. Catalyst solution is substantially or predominantly liquid phase, although it may include vapour, on entry to the separation section. Catalyst solution comprises catalyst in crude MEG. In the separation section, heat input to a temperature as hereinafter described preferably generates a flash separation of crude MEG whereby vapour phase crude MEG is separated from a solution of greater than 0 wt % to 95 wt % catalyst in crude MEG which is recycled for further use in the EO to MEG conversion reaction. As hereinbefore described, the vapour phase crude MEG is fed to the rectification section where mass transfer between liquid phase and vapour phase confers a rectification, separating MEG as overhead from diethylene glycol (DEG) and higher boiling glycols. Separated MEG rises to a pasteurisation section where further mass transfer between the phases confers a separation of MEG from an overhead stream of lower boiling residual water and other light components.

The process of the invention includes a stripping section which is preferably conducted on a liquid feed from the rectification section comprising MEG, DEG and higher glycols. Reference herein to higher glycols is to triethylene glycol and higher substituted glycols. The stripper provides an overhead vapour return which is concentrated further in MEG compared to the feed.

The liquid feed is preferably a liquid bottom product rundown from the rectification section, directly rundown to the internal stripping section or rundown to the side stripping section. The top vapours from the stripping section rise to the rectification section or are returned to the MEG purification column and, combined with the crude vapour from the catalyst separation section, are fed to the rectification section. The stripping section is operated at subatmospheric pressure of $0.5 \times 10^5$ Nm$^{-2}$ or less but higher than the rectification section. This arrangement avoids the need for a mechanical transport device between the stripping and rectification sections.

The stripping section provides a bottoms stream of concentrated DEG and higher glycols to an MEG recycle column which recovers MEG from concentrated DEG and higher glycols. In a further advantage of the invention, the reduced pressure operation in the side stripper allows reduced temperature operation in the side stripper bottoms, which minimises thermal degradation of MEG and also enhances separation. The DEG and higher glycols content of the side stripper bottoms is increased compared to the feed whereby a reduced loading of MEG is sent to the MEG recycle column. The reduced load MEG recycle compared to the prior art provides advantages in terms of favourable operating costs and plant construction costs.

Preferably, heat used in the catalyst separation section and stripping section is recovered in the overhead from the pasteurisation section. A low pressure steam generator may be operated as the pasteurisation section overhead vapour stream condenser or the overhead condenser may be used to heat up another utility or process stream. The process and apparatus of the invention is thereby operated with energy recovery from the pasteurisation section overhead comparable to that of prior art systems, despite operating at lower pressure. This allows a higher fraction of the total energy input required for MEG separation and purification to be operated in the stripping section which energy is recovered in the MEG purification column overhead condenser, allowing a higher recovery of MEG in the stripping section, but without thermal degradation thereof by virtue of the reduced pressure operation.

This is useful since energy that is used for recovery of MEG in the MEG recycle column cannot be recovered since the operating temperature is too low. This makes it attractive to recover as much as possible MEG in the stripper since that energy can be recovered for a useful benefit. More MEG going to the MEG recycle column means a lower fraction of the energy recovered in the MEG purification column condenser.

There is a balance between reducing pressure to reduce separator temperature and preserve MEG product and catalyst, and to reduce stripper bottoms temperature and load and MEG recycle load, against maintaining pressure to enable sufficient energy recovery in the pasteurisation section overhead. Preferably, the process is operated with pressures in the respective separation, rectification, stripping and pasteurisation sections which are, at the lowest, at least $0.01 \times 10^5 \, Nm^{-2}$, more preferably at least $0.02 \times 10^5 \, Nm^{-2}$, and especially at least $0.05 \times 10^5 \, Nm^{-2}$. Preferably, the process is operated with pressures in the respective separation, rectification, stripping and pasteurisation sections which, at the highest, are at most $0.5 \times 10^5 \, Nm^{-2}$, more preferably at most $0.4 \times 10^5 \, Nm^{-2}$, and especially at most $0.2 \times 10^5 \, Nm^{-2}$.

Preferably, the rectification and pasteurisation sections and, where contained in the same column, the catalyst separation and stripping sections, are operated in an integrated manner in open pressure communication, facilitating internal feed between sections. Preferably, internal feed is driven by a pressure differential over the length of the MEG purification column, and upstream catalyst separation vessel or side stripper where present. In some instances gravity is used to facilitate feed, for example liquid side draw to a side stripper, if present. Preferably, pressure differential throughout the MEG purification column is less than $0.3 \times 10^5 \, Nm^{-2}$, preferably less than $0.1 \times 10^5 \, Nm^{-2}$, with decreasing pressure throughout the elevation of the MEG purification column.

The process of the invention is operated at subatmospheric pressure whereby operation may be at lower temperature than would otherwise be the case. Preferably, the temperature in the combined MEG purification process is at least 50° C. and at most 200° C., for example, depending on catalyst type, MEG quality and prevailing pressure, more preferably at least 100° C. and at most 170° C., which facilitates energy recovery and preserves MEG quality, and especially at least 120° C. and at most 160° C.

Referring now to the further aspect of the invention as hereinbefore defined, preferably the apparatus comprises feed inlets, outlets, internals and the like such as to confer low pressure drop, thereby meeting the limitations on allowable pressure drop.

Preferably, the apparatus comprises a liquid feed inlet to the catalyst separation section supplied from an EG dehydration unit. Any suitable feed inlet may be used, and preferably a low velocity feed inlet is used to optimize separation of flashed vapours at the inlet. Preferably, the inlet provides a large surface area to facilitate the separation of crude MEG.

The apparatus of the invention provides for flash separation of catalyst from MEG vapour in situ within the MEG purification column or in a separate vessel upstream of the column. Preferably, the catalyst separation section comprises means for heat input. Preferably, heat input is by means of a reboiler, preferably a falling film type reboiler. This has the advantage of low skin temperatures and low residence time of catalyst solution in the reboiler which limits heating of catalyst.

Separated catalyst as a concentrated solution in MEG is discharged via a bottom outlet. Preferably, the bottom outlet includes a vortex breaker.

We have surprisingly found that it is possible to feed separated crude MEG from the catalyst separation section as a vapour stream to the purification section, without the need for intermediate condensation of separated MEG, mechanical transport and reevaporation in a distillation purification. Thereby the catalyst separation may be conducted in a separate upstream vessel or in the single MEG purification column. Preferably, the catalyst separation, rectification and pasteurisation sections are of substantially equal diameter. The stripping section may be of smaller diameter than the other sections. Thereby the stripping may be conducted in a smaller diameter side stripper or in the single MEG purification column whereby a swage section may be provided between the rectifying and stripping sections, to a smaller diameter stripping section. In a particular advantage the catalyst separation section comprises a sump which is of lesser diameter than the main section whereby hold up of catalyst and residence time are minimized and heating of catalyst is thereby minimised.

In the preferred embodiment, the MEG purification column comprises a liquid outlet for liquid phase MEG, DEG and higher boiling glycols to a side stripper, and a return vapour inlet for stripped concentrated MEG, the outlet and inlet being located intermediate the catalyst separation section and rectification section. Preferably, the outlet is a gravity driven rundown.

A draw-off tray enabling passing of vapours from the catalyst separation section to the rectification section, and collecting of liquid from the rectification section for passage to the side stripper is preferably located intermediate the catalyst separation section and rectification section.

Preferably, the side stripper is of lesser diameter than the catalyst separation, rectification and pasteurisation sections of the MEG purification column, since the liquid and vapour loads in the side stripper are reduced by direct vapour feed to the rectification section and improved selectivity of the catalytic glycol reaction, in particular with reduced DEG and higher glycols load. Incorporation as a side stripper has the advantage that no large swaged section is installed between the rectification and stripping section. This has advantages of reduced unit construction costs since a more compact design can be made.

The side stripper provides an overhead outlet for stripped MEG. The side stripper comprises a bottoms outlet for concentrated DEG and higher glycols to an MEG recycle column which recovers residual MEG for recycle to the dehydrator. The MEG recycle column operates at lower pressure than the side stripper to recover MEG for recycle. In a particular advantage the side stripper recovers more MEG in comparison to the prior art process, whereby a reduced load of MEG comprised in the bottoms outlet stream is sent to the MEG recycle column. Preferably, therefore, the MEG recycle is of reduced load compared to the prior art, providing advantages of reduced operating cost and reduced plant construction cost.

The MEG purification column of the invention comprises internal vapour feeds between sections. We have surprisingly found that if it is possible to feed opposing vapour and reflux streams internally with minimum entrainment, it is possible to integrate the catalyst separation and rectification in a single vessel in the preferred embodiment as hereinbefore described. Preferably, the MEG purification column provides an MEG product rundown tray which allows passage of vapour feed from the rectification section to the pasteurisation section and provides for return of MEG from the pasteurisation section for collection as product MEG, preferably as a liquid side draw-off. The pasteurisation section is located above the MEG product outlet, together with an overhead vapour outlet for MEG, residual water and other light components, a reflux of condensed overhead product and a liquid bleed stream to remove water and the light components.

Additionally, in the preferred embodiment, the MEG purification column provides an additional rundown tray which allows passage of vapour feed from the catalyst separation section to the MEG rectification section and provides for return of liquid containing MEG, DEG and higher boiling glycols from the rectification section for draw-off to the side stripper.

Preferably, the rundown trays provide low pressure drop. Suitably, for instance, a rundown tray comprises a chimney tray, vane collector or double decker gutter collector.

The apparatus may additionally comprise internals to facilitate in separation and distribution within and between sections, for example one or more demister mats, gravity distributors and the like.

The rectification, pasteurisation, and stripping sections suitably comprise internals such as preferably structured packing, or less preferred random packing, generating a temperature profile across the elevation thereof, thereby enabling separation of MEG vapour from DEG and higher boiling glycols in the rectification section and stripping section, and separating MEG from residual water and other light components in the pasteurisation section. Temperature profile may be regulated by nature and amount and density of internals as known in the art.

Preferably, a gravity distributor provides distribution of liquid to internals in the rectification, pasteurisation, and stripping sections, enabling maximum contact of vapour and liquid, to ensure optimum rectification and pasteurisation with low pressure drop.

As hereinbefore described, the pasteurisation section comprises an overhead to a steam generating energy recovery vessel or other utility or process stream heating device, for recovery of heat input to the MEG purification column and the side stripper. Preferably, a condenser operates at subatmospheric pressure of less than $0.5 \times 10^5$ $Nm^{-2}$ and is able to recover heat of condensing the MEG purification column overhead vapours at a temperature higher than 50° C., preferably higher than 100° C., more preferably higher than 120° C. and transfer this heat for use elsewhere in the unit or in associated units.

The apparatus and process of the invention may be used in any process for the catalytic conversion of EO to MEG. Preferably, the use is in a unit or process for homogeneously catalysed conversion of EO to MEG produced by a two step process, a ketal type process (catalysed by acids) or via EC catalysed by e.g. alkali or alkaline earth metal halide, zinc, tin, alkyl amine or quaternary ammonium or the like, or any other homogeneous catalysed process.

Preferably, the system is used in a catalytic process for making MEG that comprises a step in which EO is allowed to react with $CO_2$ in the presence of a catalyst thereby effecting formation of a reaction solution containing EC, and a step in which the reaction solution is converted into an EG aqueous solution by hydrolysing EC in the reaction solution, a distillation step in which water is removed from the EG aqueous solution, and a distillation step in which purified EG and a solution containing the catalyst are obtained from the resulting EG solution by distillation.

Preferably, the catalyst in such process is a homogeneous catalyst, more preferably is an alkali metal halide such as bromide or iodide, optionally in combination with a crown ether catalyst, an alkaline earth metal halide, a homogeneous zinc catalyst, an organic tin or a germanium or tellurium compound, or preferably an alkyl amine or quaternary ammonium such as a quaternary ammonium halide or a quaternary phosphonium halide. Suitable catalysts are disclosed in U.S. Pat. No. 6,080,897 the contents of which are incorporated herein by reference. Preferably, homogeneous catalysts for the hydrolysis step converting EC to MEG include carbonates such as potassium carbonate, potassium molybdate as taught in U.S. Pat. No. 4,283,580, and the like. Many homogeneous catalysts are known for the direct conversion of EO to MEG, for example as in EP-1,484,300-A1, the contents of which are incorporated herein by reference.

Preferably, the invention is for use in a process wherein conversion to MEG, DEG and higher glycols is substantially 100%, whereby there is substantially no intermediate, such as EC, to be separated. Preferably, the process is highly selective for MEG.

Figure 2:
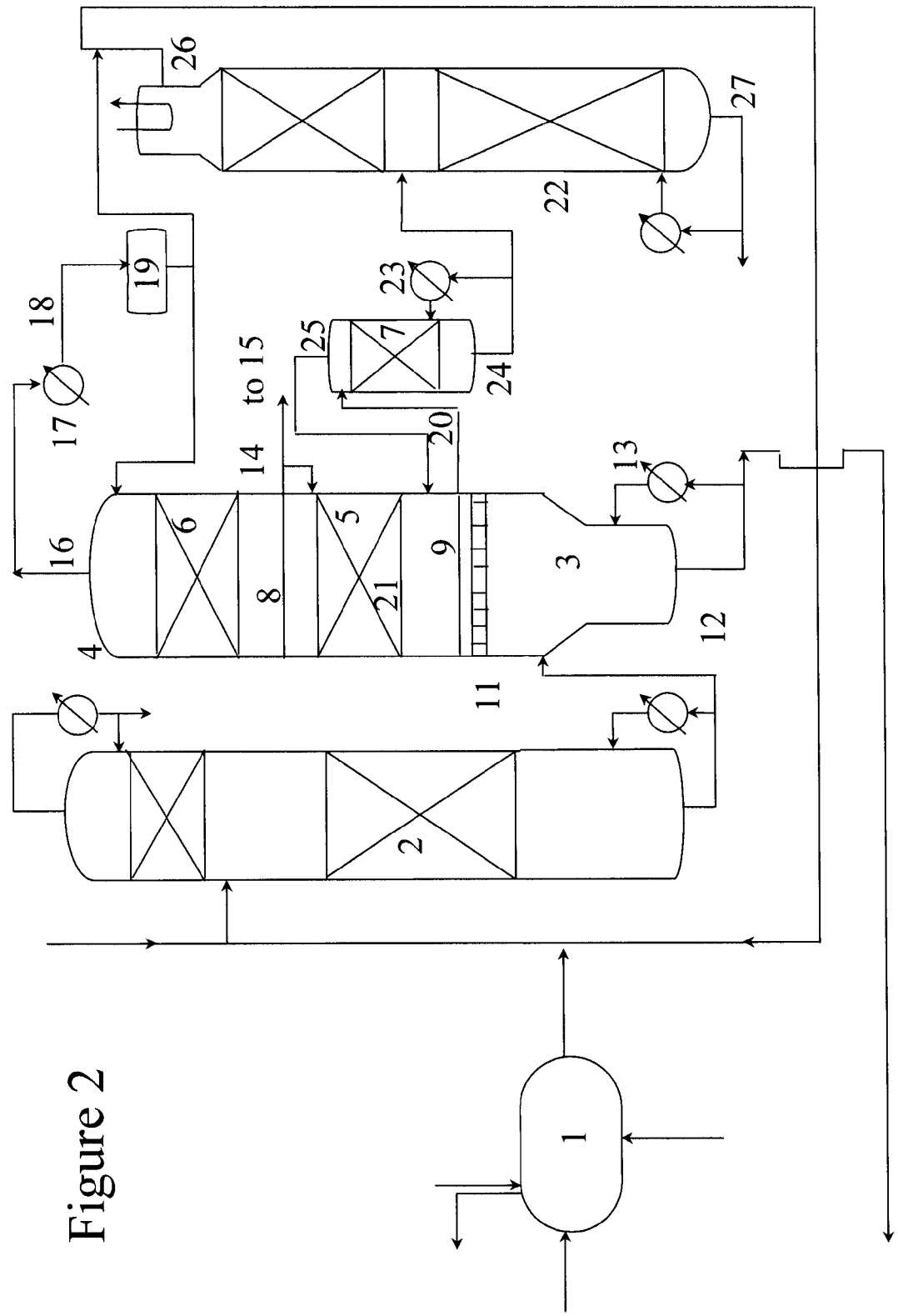
FIGS. 2 and 3 illustrate embodiments of the MEG purification process and apparatus of the invention.
Figure 3:
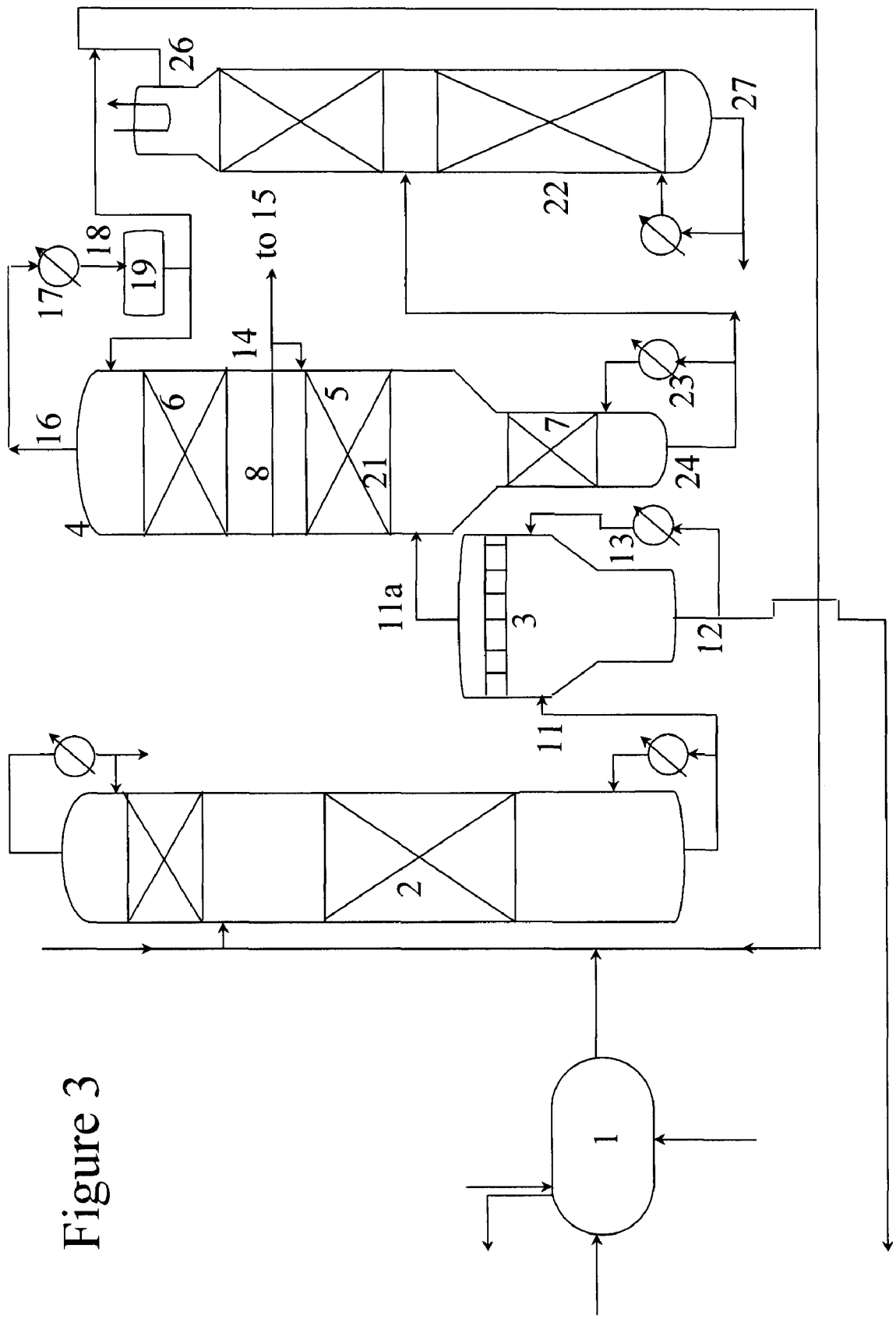

The invention is now illustrated in non-limiting manner with respect to the following Figures wherein:

FIG. 1 illustrates a MEG purification process and apparatus as shown in U.S. Pat. No. 6,080,897;

FIGS. 2 and 3 illustrate embodiments of the MEG purification process and apparatus of the invention.

In FIG. 1 is shown Glycol reactor (1), EG dehydration unit (2), catalyst separation (flash) vessel or evaporator (3), and MEG purification column (4) incorporating stripping section (7), rectification section (5) and pasteurisation section (6). Condensed liquid from the flash vessel (3) is accumulated in a drum (not shown) and then transported, either pumped or under gravity, to the column (4).

In FIG. 2 is shown Glycol reactor (1), EG dehydration unit (2), MEG purification column (4) incorporating catalyst separation section (3), MEG rectification section (5) and pasteurisation section (6). MEG side stripper is shown (7) and MEG recycle column (22). Each of EG dehydration unit (2), MEG purification column (4), MEG side stripper (7) and MEG recycle column (22) incorporate a reboiler as shown. Dehydrator (2) and MEG recycle column (22) incorporate a cold water condenser at the overhead.

Referring to FIG. 2, the glycol dehydrator bottoms contain mostly MEG, some catalyst and a minor amount of DEG and are routed to MEG purification column (4). This vacuum column operates at subatmospheric conditions and consists of bottom catalyst separation section (3), middle rectification section (5) and top pasteurisation section (6) that are separated by total liquid draw-off trays (8, 9). In the bottom catalyst separation section (3) most of the MEG present in the column feed (11) is vaporised. A concentrated catalyst solution in MEG is recovered as bottoms stream (12) and recycled back into the process, e.g. to an EC reactor (not shown) via catalyst recycle pump (not shown).

Heat input to the MEG purification column occurs via catalyst separator falling film reboiler (13).

The top section of the MEG purification column (4), the pasteurising section (6) contains packing and separates residual water and other light components, removed as overhead (16) from MEG product. High purity MEG is recovered as a liquid side stream (14) and conveyed to purified MEG storage (15).

Vapours from the overhead (16) of MEG purification column (4) are condensed in a condenser (17) that generates Low Pressure Steam or heating of another medium. The condenser has a low temperature difference that requires careful control of pressure in the column. Overheads condensate (18) from the MEG purification column (4) is collected in MEG purification column reflux drum (19) from where it is routed to the glycol dehydrator (2) for removal of water and other light components. Part is returned to the MEG purification column (4) as reflux.

The middle rectification section (5) of the MEG purification column (4) contains packing and separates MEG from DEG plus heavier components. DEG and heavier components accumulate in the lower part (21) of the rectification section (5) of the MEG purification column (4) and are removed from the column via a total liquid draw-off tray (9)

as side stripper feed (20). MEG is further concentrated in MEG side stripper (7) and DEG and heavier glycols are separated from the MEG in the MEG side stripper (7) and MEG recycle column (22). The stripper (7) bottom temperature is controlled by controlling steam flow to MEG side stripper reboiler (23), a falling film reboiler driven by steam or other heating medium.

MEG side stripper (7) is a vacuum column operating at top conditions of slightly less vacuum than the MEG purification column and has a bed of packing. The side stripper (7) concentrates DEG and heavier components in the side stripper bottoms (24). Side Stripper overhead (25) vapour, mainly MEG, is returned to the rectification section (5) of the MEG purification column (4).

MEG recycle column (22) is a vacuum distillation column that operates at top conditions at the internal condenser of deeper vacuum than the MEG purification column. The column recovers residual MEG that is present in the MEG side stripper bottoms stream (24). The recycle column (22) comprises packing. Heat input is by falling film type reboiler driven by steam or other heating medium. The column incorporates an overhead condenser, in this case as an internal condenser to reduce pressure drop. Liquid from the condenser is collected on a liquid draw-off tray that can also act as an accumulator. MEG is recovered as MEG recycle column top (26) product and is recycled to the glycol dehydrator (2) where any light decomposition products are removed. The MEG recycle column bottoms (27) contains highly concentrated DEG and is discharged to storage for further processing.

FIG. 3 shows an alternative embodiment to FIG. 2 in which catalyst separation section (3) is located upstream of MEG purification column (4), MEG purification column comprising stripping section (7), rectification section (5) and pasteurisation section (6) in stacked design. Stripping section (7) is of smaller diameter than rectification (5) and pasteurisation (6) sections, there is a swaged section between the stripping (7) and rectification (5) sections. Vapour feed is provided by side entry inlet (11a) from the catalyst separation section (3) to intermediate the stripping (7) and rectification (5) sections. DEG and heavier components accumulate in the lower part (21) of the rectification section (5) of the MEG purification column (4), as in FIG. 2, but in this embodiment are not removed from the column but are fed to the stripping section (7).

The MEG purification column, separate catalyst separation vessel and MEG side stripper where present, and MEG recycle column are operated under subatmospheric conditions. Because of limitations on allowable pressure drop over the columns, low pressure drop packing is employed. Suitable packing has low liquid hold-up. Falling film reboilers are also selected for all columns, in order to minimise thermal decomposition of the MEG product or the catalyst.

Plant construction cost advantages consist of a compact MEG purification column design (FIG. 2) or to a lesser extent a swaged design (FIG. 3) and a reduced size of MEG recycle column design and associated equipment. Operating savings are achieved since relatively more energy required for MEG separation is recovered at the MEG purification condenser and an extra energy input is avoided by introducing the crude MEG stream as a vapour to the rectifying section directly from the catalyst separation section.

What is claimed is:

1. A process for the separation of a homogeneous catalyst solution from crude monoethylene glycol and for purifying the crude monoethylene glycol, for use in a process for the catalytic conversion of ethylene oxide to monoethylene glycol, which process comprises:
    separating the catalyst solution in a catalyst separation section by evaporating crude monoethylene glycol; and
    purifying the crude monoethylene glycol by feeding the crude monoethylene glycol to a rectification section, a stripping section, and thence to a pasteurisation section, wherein
        each section is operated at subatmospheric pressure of $0.5 \times 10^5$ $Nm^{-2}$ or less, the rectification and pasteurisation sections being at pressure less than that of the catalyst separation section;
        the process provides a pressure differential between the catalyst separation and rectification sections; and
        the vapour phase crude monoethylene glycol from the catalyst separation section is fed as substantially vapour phase feed to the rectification section.

2. The process as claimed in claim 1, wherein the pressure of each section is in the range of from $0.02 \times 10^5$ $Nm^{-2}$ to $0.4 \times 10^5$ $Nm^{-2}$.

3. The process as claimed in claim 1, wherein the pressure of each section is in the range of from $0.05 \times 10^5$ $Nm^{-2}$ to $0.2 \times 10^5$ $Nm^{-2}$.

4. The process as claimed in claim 1, wherein the separation, rectification and pasteurisation sections are located in a monoethylene glycol purification column and operate with internal feeds in open pressure communication between the sections and the stripping section is located externally to the monoethylene glycol purification column and is operated as a side stripping section at subatmospheric pressure greater than the pressure of the rectification section, with an external feed in open pressure communication with the rectification section.

5. The process as claimed in claim 4, wherein condensed liquids from the rectification section are fed externally to the stripping section and stripped monoethylene glycol vapours are returned externally to in between the separation and rectification sections.

6. The process as claimed in claim 4, wherein the internal feed is driven by a pressure differential over the length of the monoethylene glycol purification column and the side stripper.

7. The process as claimed in claim 1, wherein the stripping, rectification and pasteurisation sections are located in a monoethylene glycol purification column and operate with internal feeds in open pressure communication between the sections and the stripping section is installed below the rectification section, and the catalyst separation section is located externally to the monoethylene glycol purification column and is operated with an external feed in open pressure communication with the rectification section.

8. The process as claimed in claim 7, wherein the vapour phase crude monoethylene glycol from the catalyst separation section is fed externally to in between the stripping and rectification sections.

9. The process as claimed in claim 7, wherein the internal feed is driven by a pressure differential over the length of the monoethylene glycol purification column and the upstream catalyst separation vessel.

10. The process as claimed in claim 1, wherein heat input in the catalyst separation section and stripping section is recovered in an overhead from the pasteurisation section.

11. The process as claimed in claim 1, wherein the process is operated at temperatures in the range of from 50° C. to 200° C.

12. A process for preparing monoethylene glycol comprising:
converting ethylene oxide to crude monoethylene glycol in the presence of a homogeneous catalyst;
separating the catalyst in a catalyst separation section by evaporating crude monoethylene glycol; and
purifying the crude monoethylene glycol by feeding the crude monoethylene glycol to a rectification section, a stripping section, and thence to a pasteurisation section, wherein each section is operated at subatmospheric pressure of $0.5 \times 10^5$ Nm$^{-2}$ or less, the rectification and pasteurisation sections being at pressure less than that of the catalyst separation section;
the process provides a pressure differential between the catalyst separation and rectification sections; and
the vapour phase crude monoethylene glycol from the catalyst separation section is fed as substantially vapour phase feed to the rectification section.

* * * * *